(12) United States Patent
Weksel et al.

(10) Patent No.: US 11,246,995 B2
(45) Date of Patent: Feb. 15, 2022

(54) HOLLOW NEEDLE AND PIVOTABLE HUB SYSTEM

(71) Applicant: Jasperate, Inc., Lisle, IL (US)

(72) Inventors: David Weksel, Lisle, IL (US); Stephen Soloway, Vineland, NJ (US); Charles S. Brunner, North Reading, MA (US)

(73) Assignee: Jasperate, Inc., Lisle, IL (US)

(*) Notice: Subject to any disclaimer, the term of this patent is extended or adjusted under 35 U.S.C. 154(b) by 541 days.

(21) Appl. No.: 15/942,961

(22) Filed: Apr. 2, 2018

(65) Prior Publication Data

US 2019/0298938 A1 Oct. 3, 2019

(51) Int. Cl.
| | |
|---|---|
| *A61M 5/34* | (2006.01) |
| *A61M 25/00* | (2006.01) |
| *A61M 25/06* | (2006.01) |
| *A61M 5/32* | (2006.01) |

(52) U.S. Cl.
CPC .......... *A61M 5/343* (2013.01); *A61M 5/3245* (2013.01); *A61M 25/0097* (2013.01); *A61M 25/0606* (2013.01); *A61M 25/0612* (2013.01)

(58) Field of Classification Search
CPC ........ A61M 5/343; A61M 5/34; A61M 5/158; A61M 5/28; A61M 5/24; A61M 5/32; A61M 5/3293; A61M 5/344; A61M 5/347; A61M 2005/341; A61M 2005/342; A61M 2005/1581; A61M 25/0097; A61M 25/0606; A61M 25/0612; A61B 90/11
See application file for complete search history.

(56) References Cited

U.S. PATENT DOCUMENTS

| | | | |
|---|---|---|---|
| 2,853,070 A * | 9/1958 | Julliard | A61M 5/20 604/224 |
| 5,405,330 A * | 4/1995 | Zunitch | A61M 5/34 604/240 |
| 10,086,193 B2 * | 10/2018 | Schulte | A61N 1/0539 |

* cited by examiner

*Primary Examiner* — Tiffany Legette
*Assistant Examiner* — Antarius S Daniel
(74) *Attorney, Agent, or Firm* — Latimer LeVay Fyock LLC (57) ABSTRACT

A needling system, for use in areas where thin hollow needles are used to inject or aspirate fluids and gases, is provided and comprises a thin, rigid tube body needle that is open on both ends and throughout the length with one sharp end. The needle body and hub are designed such that the needle has a ball end that fits within a socket of the hub, forming a seal and allowing the needle to be oriented non-colinearly and non-parallel to the central axis of the hub. Needle orientation, relative to the hub, can be limited from a conical volume to a planar or multi planar angular orientations. The needle so configured allows the user to circumvent an obstacle that otherwise inhibits direct linear access to a point-of-interest by providing a device that can fit around or between obstructions providing optimal direct path towards the desired therapy delivery point.

10 Claims, 12 Drawing Sheets

HOLLOW NEEDLE AND PIVOTABLE HUB SYSTEM

FIELD OF THE INVENTION

The present invention concerns a needle and a hub system. More particularly the present invention concerns a combination of a straight hollow needle and a hub having pivoting means to allow the needle to avoid blockages and penetrate skin, or other surfaces, and reach a point therewithin. The blockages avoided can include those that would block the needle or that could keep the needle from reaching the point of interest by blocking the syringe or other device attached to the needle.

BACKGROUND OF THE INVENTION

Penetration of the skin, or other surfaces, to deliver fluids, or other products, or to aspirate such from within the surface is well known. Penetration is typically done using a hollow needle in combination with any one of a variety of known devices, including but not limited to hypodermic needles. A hypodermic needle is defined as a thin tube inserted into a vein or body cavity to enable a number of different actions, including but not limited to administering medication, draining off fluid, or inserting a surgical instrument. These needles are traditionally straight, thin, hollow tubes with a sharpened tip at one end. Some variations include needles with distal openings of extended length to provide more rapid movement of fluids and other materials, extended length needles allowing deeper penetration before fluid and other material actions (such as needles used to administer adrenaline into the heart during cardiac episodes) and needles having smaller length for subcutaneous actions. Commonly used with syringes, needles provide a means to penetrate human and or other animal tissue or synthetic materials to create a pathway to target a point-of-interest. The needle and syringe combination enables the user to aspirate and or inject medication and or to draw bodily fluids such as sanguinous, serosanguineous, purulence, exudates and transudate. It should be noted that in some applications a desired action can be accomplished without the use of a syringe but by use of the needle alone or by integration of the needle with some other means of causing the action. A traditional hypodermic needle includes a straight, hollow needle tube and a leading cutting edge. Further, such needles are typically used in conjunction with a means of injecting or extracting fluids to and from a point-of-interest.

As an example, the classic combination of a needle and syringe can be considered a "needling system". The syringe and needle are typically connected in a manner that fixes the position of the needle relative to the syringe where the needle and syringe are co-axial or in some instances the needle and syringe while not being co-axial are parallel. It should be noted that the diameter of the needle is significantly smaller than that of the syringe. As configured, this needling system is typically restricted to a direct line access from a surface to a point therewithin, with little variation in the direction or path. Typically, a straight needle is aimed from the surface so as to find its way, through a straight line, to a targeted position; the syringe is on that same line of access but is of significantly larger diameter than the needle. In such a case access to the target area is not only restricted by the ability of the needle to move in a straight line to the target area, but also by the ability of the syringe to bypass any potential restrictions that are exterior to the surface to be pierced.

The art of needles and needle systems for use in medical procedures has advanced little beyond the earliest uses of puncturing the skin to arrive at a straight-line position for insertion or removal of fluids. Experimental uses of hypodermic needles for medical purposes were first performed in 17th century. However, due to poor results the technology was largely dormant until the 19th century when more appropriate materials and construction techniques became available; uses also improved with the realization and implementation of sanitary conditions for medical procedures. Today, due to significant advances, hypodermic needles have emerged as a critical component of medical care worldwide.

However, a significant drawback with the traditional hollow needle and needling system, as typically configured, continues to thwart their use in new and medically significant ways. Disadvantageously, in the use of traditional needles and needling systems, there exists the problem that in the event of an obstruction either below or above the skin, the needle and/or needling system cannot easily access the point-of-interest below the skin or other tissue that requires the aspirating, injecting or aspiration. For example, in the medical field, a traditional straight hypodermic needle may fail when a patient has metal and or other implants embedded under the skin and or when a tendon and or other sensitive tissue blocks straight access to a joint or another point-of-interest that needs to be aspired or injected or drawn. Another example is when a patient has mobility issues or items on the outside of the skin that introduces difficulties in accessing the point-of-interest, the use of a straight needle may not give appropriate access requiring time to position the patient or remove the item blocking access to the detriment of the emergency care of the patient. Further, the structure of the body and or limits on that structure due to disease may create situations where a body part impairs access to the point of interest Health care workers have been known to manually bend or otherwise manipulate the needle to enable access. However, surgical grade steel is typically not easy to manipulate and small tubes can be blocked or kinked by such manipulation such that they cannot work or work poorly. More typically, the health care worker attempts to manipulate the needle so as to angle the straight needle around the obstruction. Unfortunately, these practices usually require using a longer and perhaps wider needle, potentially causing damage to delicate arterial, venal or other structures. Additionally, bending of the instrument by the healthcare worker puts the worker at risk of injury by having to manipulate a sharp object in an unintended/off label manner. The costs to the health care worker and patient include the added time requirements while safety and maintaining manufacturing and structural integrity issues may arise. In addition, this can lead to inhibited flow through the needle and additional patient and health care worker trauma from the use of a larger needle.

It would be desirable to have a system that allows the user to decide and manipulate a single device at the time of use to manipulate the needling system so that obstacles can be avoided and so that the user successfully places the needle at the point of interest without having to change the device in hand, thereby saving time, effort and money as will be described below.

It is therefore an object of the present invention to provide a device and means to access a point-of-interest in a body, where direct access to the point has been blocked by generally either impenetrable obstacles or obstacles that cause part or all of prior art penetration equipment to be blocked. Further, it is an object to provide a device that can be easily manipulated to avoid such obstacles, to secure a straight-line approach with a single device. It is a further object of the present invention to provide a medical professional with alternative means to provide rapid and accurate health assistance in normal and emergency situations where obstructions would normally thwart the use of hypodermic needles. Other objects and advantages of the present invention will become apparent as the description proceeds.

SUMMARY OF THE INVENTION

In accordance with the present invention, a needling system is provided comprising a hollow needle having a distal end and a proximal end, a hub comprising means to hold the proximal end of the hollow needle at a distal end of the hub when connected thereto. The hub being receptive to connection to a supply device at a proximal end of the hub; the hub and needle sharing a longitudinal axis therethrough when connected and in a first coaxial position. Wherein the needle is pivotable, at its proximal end within the hub, such that the distal end of the needle can be placed at an acute angle relative to the longitudinal axis of the hub. It will be understood by persons having ordinary skill in the art, that the supply device can be any device that can attach to the hub to contribute to either pushing matter out through the hub and needle, or drawing matter into the needle and hub.

In a preferred embodiment of the needling system, the needle comprises an upper section defining a first opening and a sharpened point defining a second opening with a shaft therebetween, the tube defining a longitudinal axis therethrough and having at least one lumen extending from the upper section to the sharpened point. The hub contains a ball having a hole therethrough so as allow the needle to be secured and provide a pass through for matter and the hub comprises a means for locking the angular position of the needle relative to the hub. In the preferred embodiment, the means for locking comprises a locking ring and a cooperative socket seat for seating the ball, the locking ring being attachable to the socket seat. In the operation of the device then, when the ball with a needle attached thereto is placed in the socket seat and the locking ring is placed on the socket seat, the needle shaft can be positioned as desired and the locking ring then turned to force the ball against the socket and lock the needle shaft in place in a selected position.

In another embodiment, the locking ring and cooperative socket each comprise cooperative inclined planes such that when the locking ring is rotated relative to the locking socket the ring and socket are alternatively pushed together or pulled apart depending on the direction of rotation. It will be seen that generally the hub comprises a geometry that tends to limit the angular position of the needle, relative to a main axis of the hub, to positions within a generally conical shape about the edge of the hub.

Additionally, the needling system can be made such that the locking system comprises means to confine rotation to a single plane relative to a main axis of the needling system. In such embodiments, the means to confine rotation comprises a generally spherically shaped hood having a needle width slit therein, the slit being made generally perpendicular to the axis of the hub, such that when the hood, needle and ball are attached to the hub the needle can be pivoted away from the hub axis only within the slit.

In summary, the present invention discloses a needling system that comprises a hollow needle having a distal end and a proximal end; a ball having a hole therethrough so as allow the needle to be secured thereto at its proximal end and to provide a pass through for matter; a hub comprising means to hold the ball and the proximal end of the needle at a distal end of the hub when connected thereto, and receptive to connection to a supply device at a proximal end of the hub, the hub and needle sharing a longitudinal axis therethrough when connected and in a first coaxial position. Additionally, the present invention can have a hub that further comprises a locking ring and a cooperative socket seat for seating the ball, the locking ring being attachable to the socket seat such that when the ball and needle are placed in the socket seat and the locking ring is placed on the socket seat, the needle shaft can be positioned as desired and the locking ring then turned to force the ball against the socket and lock the needle shaft in place in a selected position at an acute angle relative to the longitudinal axis of the hub. The locking of the needle in place occurs when the locking ring is turned to force the ball against the socket. The invention can include that the locking ring and cooperative socket each comprise cooperative inclined planes such that when the locking ring is rotated relative to the locking socket the ring and socket are alternatively pushed together or pulled apart depending on the direction of rotation. Additionally, the hub can comprise means to confine rotation to a single plane relative to a main axis of the needling system. Such means can include a generally spherically shaped hood for the hub, the hood having a needle width slit made generally perpendicular to the axis of the hub, so that when the hood, needle and ball are attached to the hub the needle can be pivoted away from the hub axis only within the slit.

A more detailed explanation of the invention is provided in the following description and claims and is illustrated in the accompanying drawings.

BRIEF DESCRIPTION OF THE DRAWINGS

A better understanding of the present invention may be obtained with reference to the following description in conjunction with the drawings in which.

DETAILED DESCRIPTION OF THE ILLUSTRATIVE EMBODIMENT

While the present invention is susceptible of embodiment in various forms, there is shown in the drawings a number of presently preferred embodiments that are discussed in greater detail hereafter. It should be understood that the present disclosure is to be considered as an exemplification of the present invention, and is not intended to limit the invention to the specific embodiments illustrated. It should be further understood that the title of this section of this application ("Detailed Description of the Illustrative Embodiment") relates to a requirement of the United States Patent Office, and should not be found to limit the subject matter disclosed herein.

Figure 1:
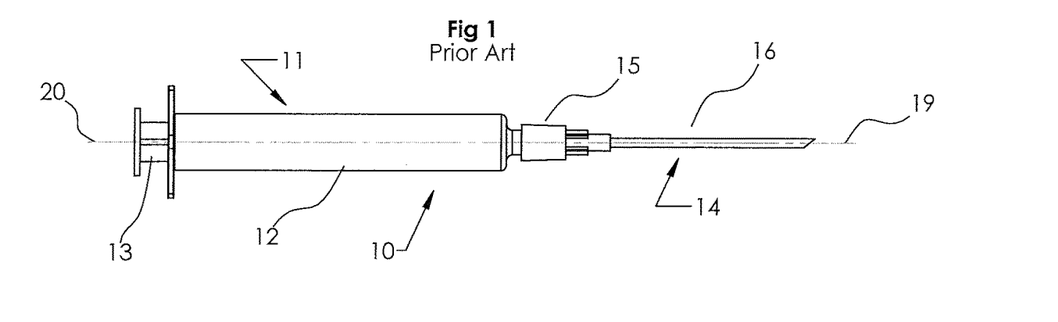
FIG. 1 is a front elevational view of a hollow needle and needling system of the prior art.
Figures 1A, 1B:
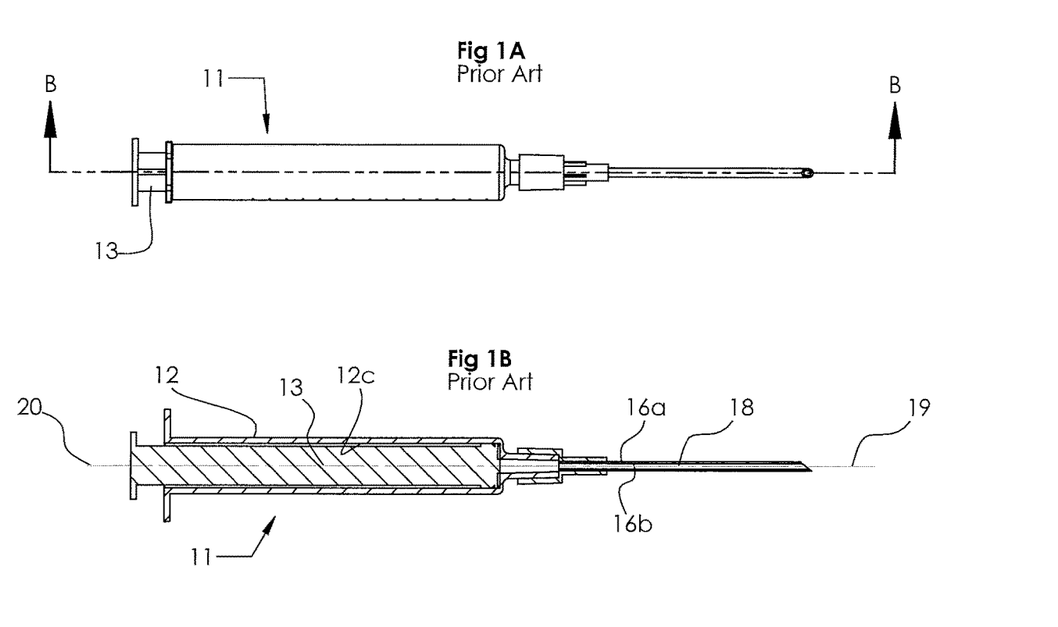
FIG. 1A is a top elevation view of the hollow needle and needling system of the prior art.
FIG. 1B is a cross sectional view of the hollow needle and needling system of FIG. 1, taken along the line B-B of FIG. 1A.

To better understand the issues in prior art needling systems, a brief review of such and the methods of using them wherein problems of accessing a point of interest are here reviewed. Referring to FIGS. 1, 1A and 1B, a needling system or cannula system 10 of the prior art is shown; it will be understood by persons having ordinary skill in the art that needling systems 10 are typically made of multiple parts: the syringe 11, consisting of two major parts, the body 12 and the plunger 13; and the needle 14 consisting of three parts, the hub 15, the shaft 16 and the bevel 17. The hub 15 is at one end of the needle and is the part that bridges between the needle and a syringe or other medical apparatus, attaching thereto. The shaft 14 is the long slender stem of the needle 14 that is beveled 17 at one end to form a point. The hollow bore of the needle is known as the lumen 18. Needle 14 is generally cylindrical and comprises an inner generally cylindrical hollow section or lumen 18 therewithin, running the entire length of the needle 14. FIG. 1B, shows a cross-sectional view of the needling system, including the exterior surface 16a of the needle shaft 16 and interior surface 16b of the hollow section 18 of the needle shaft 16. It will be seen that the shaft 16 of the prior art needle 14 is generally straight and when used as designed, provides access to, among other things, the interior of a body by means of puncturing the skin or other barrier, and thereby providing straight line access between an item connected to the needle and a body and that the centerline 19 of the needle shaft 16 is parallel and typically co-linear with the center line 20 of the attached device 11, in this example a syringe 11.

Figure 2:
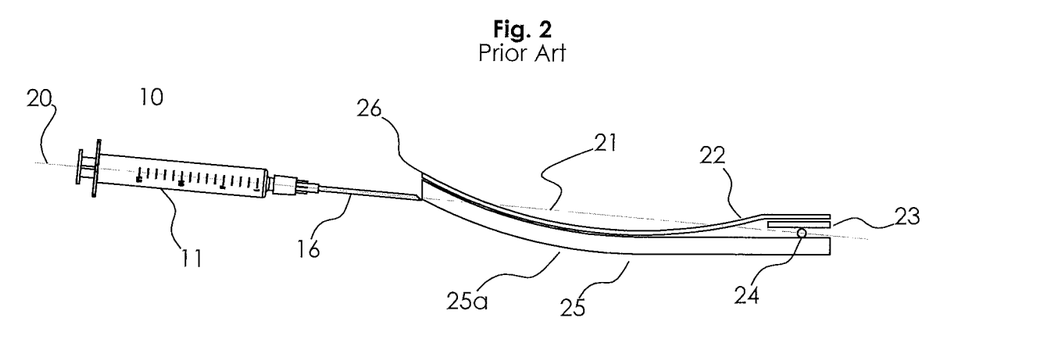
FIG. 2 is a front elevational view of a prior art hollow needle and needling system in use.

Referring now to FIG. 2, to illustrate some of the problems with the prior art needling systems, a typical prior art needling system 10 is shown along a desired injection line 21 being used to access a point of interest 24. To access point of interest 24, skin (or other membrane) 22 must be pierced and both obstructions 23 and 25 must be avoided. As shown in FIG. 2, obstruction 25 may not be linear, having some bend 25a which may occur as either a part of a single obstruction (as shown) or may occur as, for example, a joint or other obstruction (not shown). The illustrated curve 25a in the obstruction 25 causes it to block access to point of interest 24 making it impossible for the illustrated prior art needling system 10 to access point of interest 24.

Figure 2A:
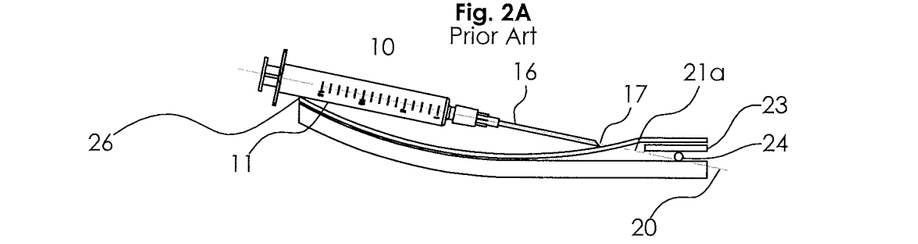
FIG. 2A is a front elevation view of prior art hollow needle and needling system in use.
Figure 2B:
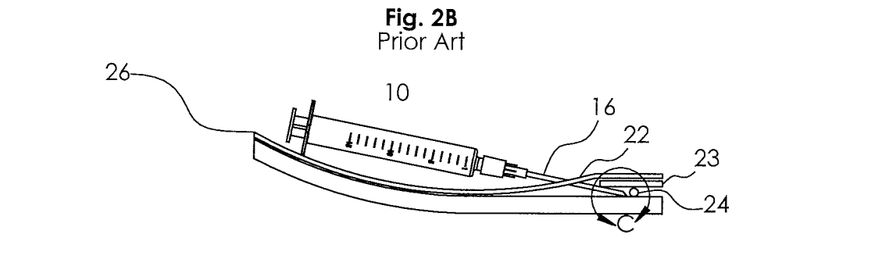
FIG. 2B is a front elevation view of prior art hollow needle and needling system shown with the needle inserted.
Figure 2C:
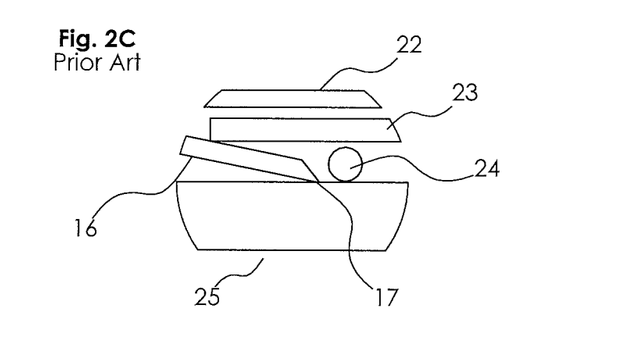
FIG. 2C is a detailed schematic representation of the tip of a prior art hollow needle and needling system in relation to a hard to reach point of interest.

Now referring to FIG. 2A, the user has positioned needling system 10 in such a manner that the syringe body 11 is tangential to the obstruction's tip 26, such that needle 16 will just clear first obstruction 23. It can be seen by referring to FIG. 2B and in more detail in FIG. 2C that due to obstructions 23, 25, needle shaft 16 contacts first obstruction 23 while also having its tip 17 contact second obstruction 25. Contact occurs in such a manner that needle 16 cannot access the point of interest 24. It should also be noted that due to the limited clearance between syringe 11, skin 22 and obstruction 25, an awkward control situation is created. A person having ordinary skill in the art and having only the prior art before him, would suggest that a longer needle could be used here, such that the needle spanned the distance from obstruction tip 26 to target of interest 24, thus eliminating limits of the syringe 11. It will be understood, however, that where this solution is possible the solution would create a situation where the use of a longer needle can have a deleterious effect on the user's control of the procedure and more particularly the path and targeting of the needle. Further, when using a longer needle, a larger gauge needle may be required and can add to the trauma at the injection site.

Figure 2D:
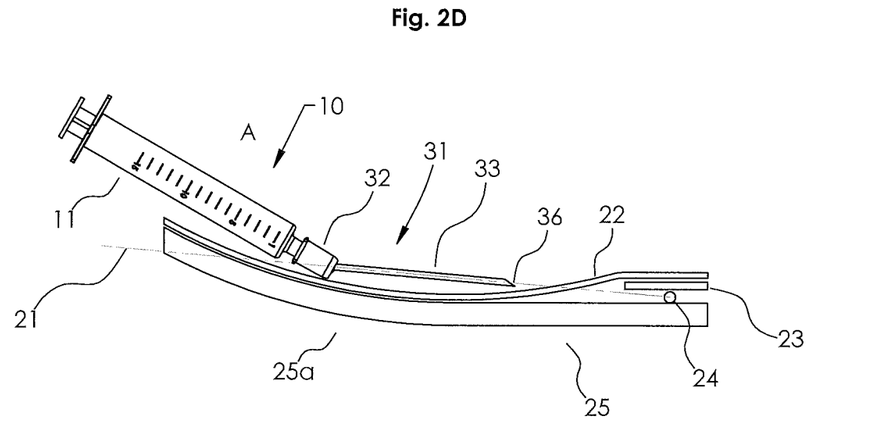
FIG. 2D is a front elevation view of one embodiment of the needling system of the present invention shown in a position allowing access to the point of interest along a desired line of injection.
Figure 2E:
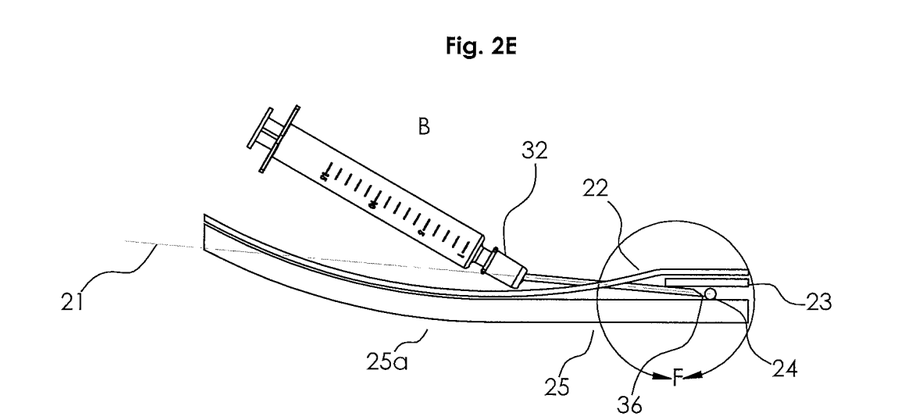
FIG. 2E is a front elevation view of one embodiment of the needling system of the present invention shown with the needle inserted along a line of injection and accessing the point of interest.
Figure 2F:
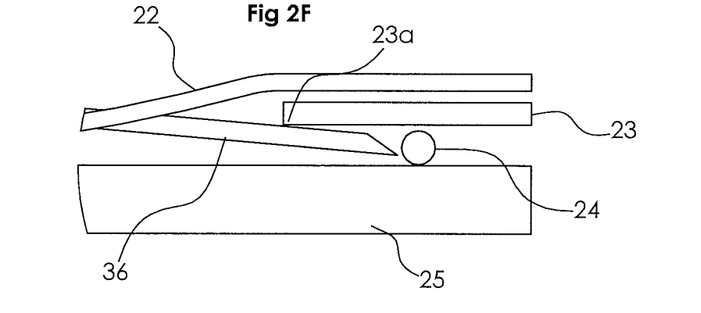
FIG. 2F is a detailed schematic representation of FIG. 2E showing the tip of the hollow needle of the present invention and the point of interest.

By contrast, the needling system 10 of the present invention has overcome the issues presented by the use of needling systems of the prior art as will be shown and described herein. Now referring to FIGS. 2D, 2E, and 2F, the present invention includes a needling system 10 comprises a syringe 11, a hub 32 and a needle 31. Needle 31, as with the prior art, comprises a shaft 33, having a lumen 34 and a sharp tip 36. In contrast to the prior art, needle 31 can be arranged, by operation of the present invention as explained in more detail below, in a non-coaxial angle relative to hub 32 and syringe 11. Referring to FIG. 2D, it can be seen that by having needle 31 in a non-coaxial relationship with hub 32, the system 10 can be fit within the same obstruction curve 25a at which the prior art, as previously illustrated, failed. As shown in FIG. 2D, at the pre-injection position A, the needling system 10 of the present invention allows non-obstructed access to the point of interest 24 along the desired line of injection 21. Referring now to FIGS. 2E and 2F, the needling system is shown to be pushed forward, to position B, by the user to puncture skin 22 along the desired line of insertion 21 avoiding both obstructions 23 and 25 and enabling the needle tip 36 to easily access the point of interest 24.

Figure 2G:
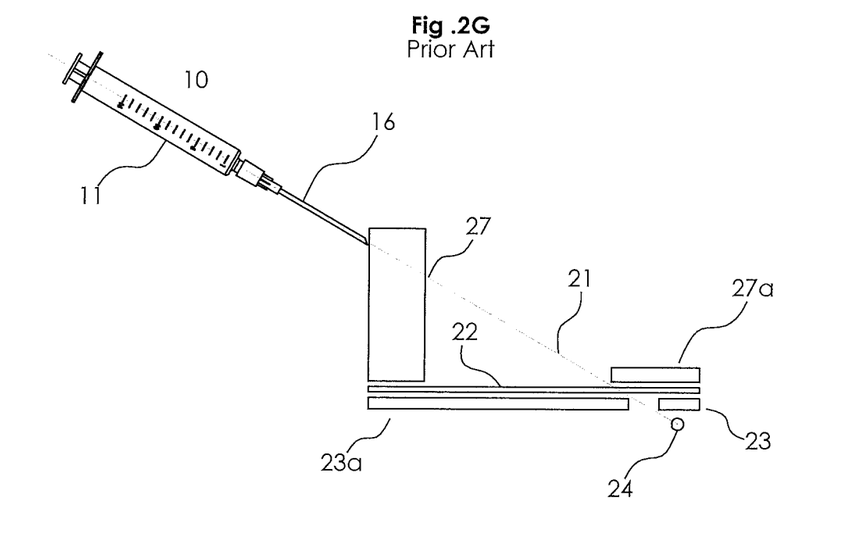
FIG. 2G is a front elevational view of prior art hollow needle and needling system.
Figure 2H:
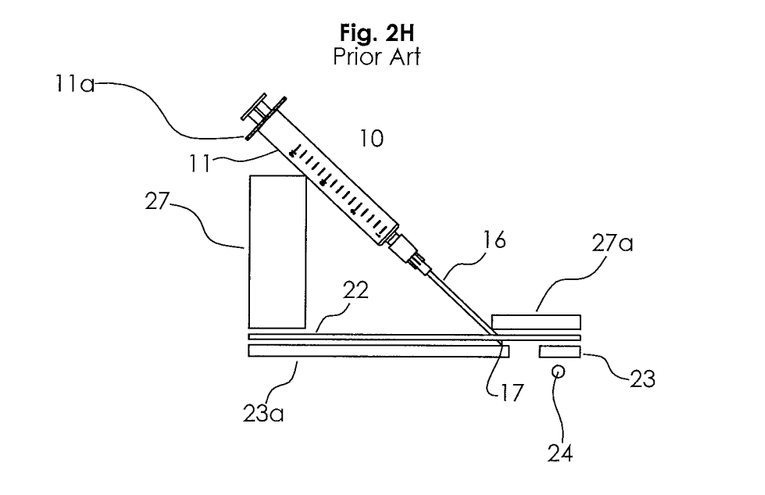
FIG. 2H is a front elevational view of prior art hollow needle and needling system.
Figure 2I:
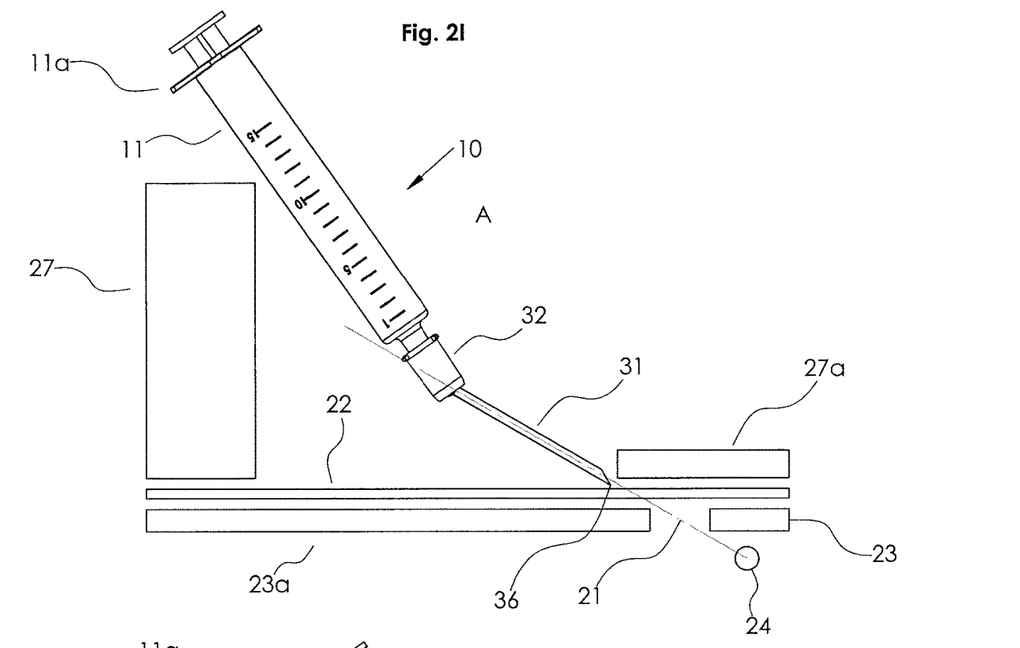
FIG. 2I is a front elevational view of one embodiment of the needling system of the present invention accessing a point of interest along a desired line of injection.

FIG. 2G depicts yet another potential obstruction configuration that may be encountered when treating patients. In this case, obstruction 27 and 27a are external to the skin 22, and obstructions 23 and 23a are internal and below the skin 22. It can be seen that with this configuration there is a desired line of injection 21. In this case obstruction 27 blocks access to point of interest 24. Now referring to FIG. 2H showing the same configuration of obstructions, a user may orient the syringe 11 such that it just clears obstruction 27, and needle 16 just clears obstruction 27a. However, due to the configuration of the obstructions the needle 16 is now oriented off the ideal line of injection and is not inline to access point of interest 24. Further, due to second internal obstruction 23a, the needle 16 cannot in this configuration penetrate deep enough to get near the point of interest 24 as the end 11a of syringe 11 will strike obstruction 27 prior to needle 16 reaching the point of interest 24.

Figure 2J:
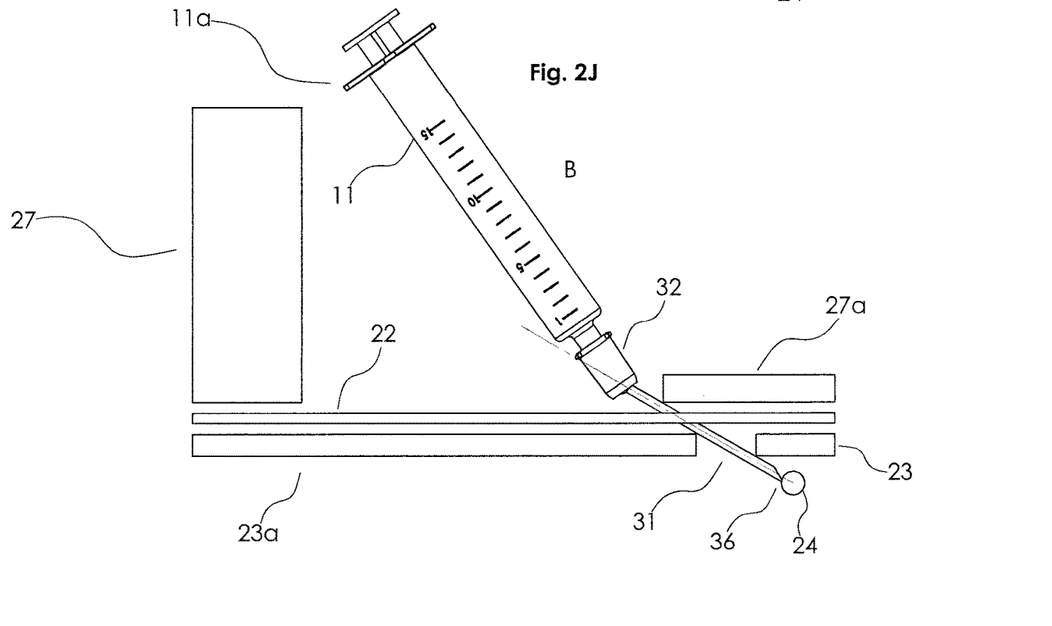
FIG. 2J is a front elevational view of one embodiment of the needling system of the present invention accessing the point of interest while avoiding internal and external obstacles.

Referring now to FIGS. 2J and 2K, the needling system 10 of the present invention is shown, comprising a hub 32 and a needle 31 having sharp tip 36, where the needle 31 is positioned, by action of the present invention as will be described in greater detail below, at a non-coaxial angle relative to the hub 32 and syringe 11. It can be seen in FIG. 2J that by having needle 31 positioned non-coaxially with hub 32, the system 10 can be positioned at a pre-injection position A allowing non obstructed access to the point of interest 24, along the desired line of injection 21. Referring now to FIG. 2K, the needling system 10 is pushed forward, to position B, by the user to puncture skin 22 along the desired line of insertion 21 avoiding obstructions 23a, and 27a and enabling the needle 16 tip 36 to access the point of interest 24. As shown, end 11a of syringe 11 does not strike obstruction 27, gliding right by without interference in the needling process.

Figures 3, 3A:
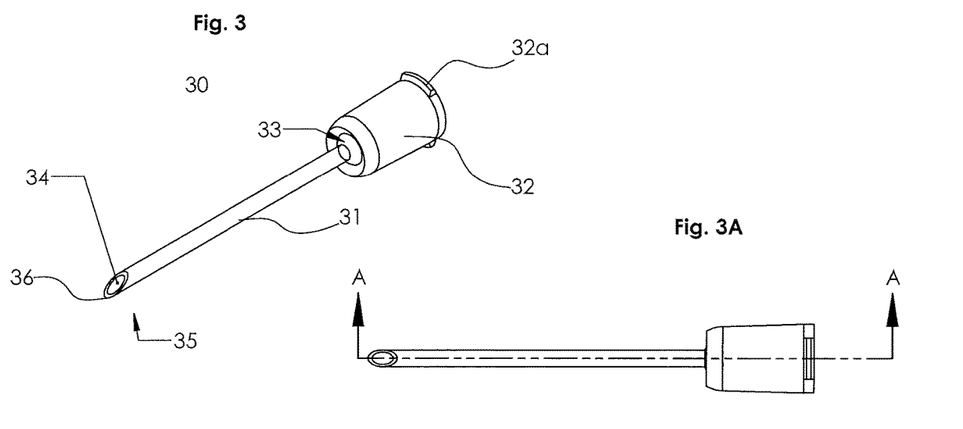
FIG. 3 is a perspective view of one embodiment of the hollow needle of the present invention.
FIG. 3A is a top plan view of the hollow needle of FIG. 3.
Figure 3B:
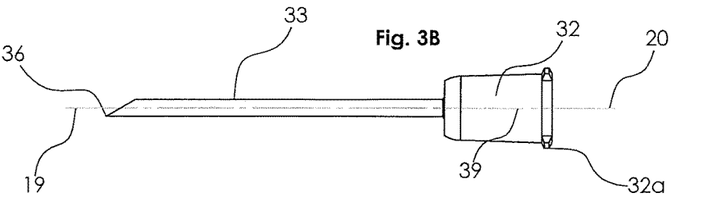
FIG. 3B is a bottom plan view of the hollow needle of FIG. 3A.
Figure 3C:
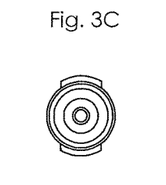
FIG. 3C is a left plan view of the hollow needle of FIG. 3B.
Figure 3D:
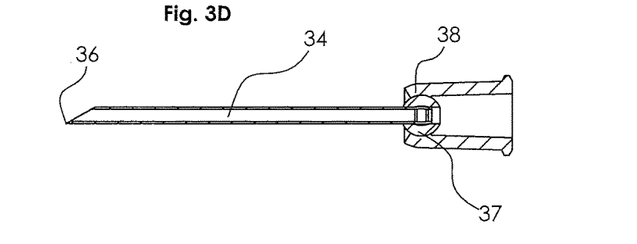
FIG. 3D is a cross-section view of the hollow needle of FIG. 3A, taken along the line A-A of FIG. 3A.
Figure 6:
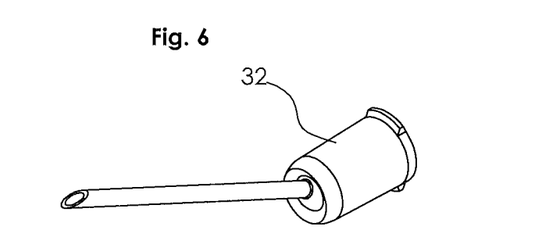
FIG. 6 is a perspective view with the needle and ball component of FIG. 5 shown in a non-co-axial orientation.
Figure 6A:
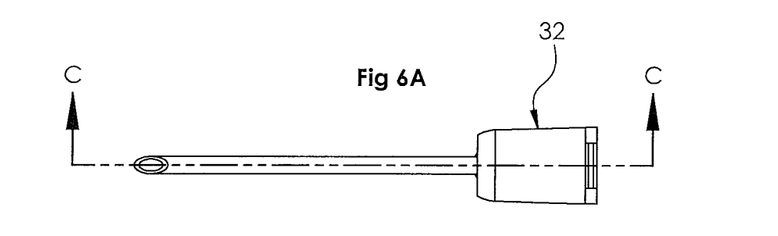
FIG. 6A is a top elevational view of the device of FIG. 6.
Figure 6B:
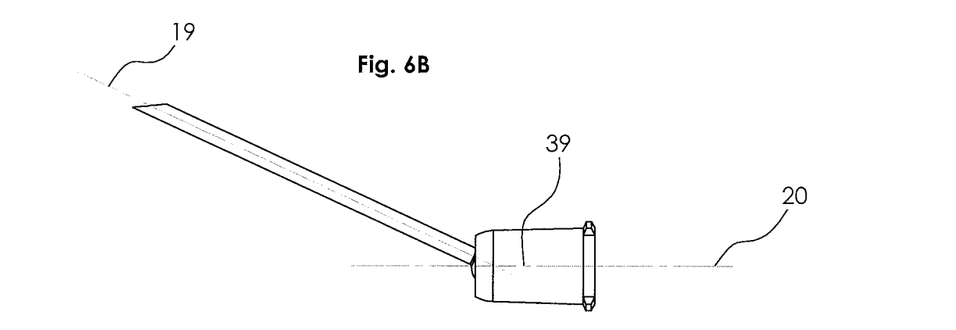
FIG. 6B is a front elevational view of the device of FIG. 6A.

Referring now to FIG. 3, a hollow needle 30, of the present invention, is illustrated comprising a thin, rigid tube body or shaft 31 receiving a hub or syringe attachment mechanism (commonly a luer lock) 32 at end 33. Although this embodiment describes the use of a luer lock, other attachment mechanisms or hubs may be used for connection of the hollow needle 30 to a syringe or other medical device as known to persons having ordinary skill in the art, without departing from the novel scope of the present invention. As will be known to persons having ordinary skill in the art, the most common connection of medical needles is the syringe; which typically comprises a cylindrical body or tube 12 within which a plunger 13 can be moved along the longitudinal axis 20 of the syringe (see, FIGS. 1 and 1B) within a cavity 12c, designed to hold or receive liquids to inject or retract a substance from or into the syringe through the lumen 34 of needle 30 to or from a point-of-interest 24 under the skin 22. At the needle shaft's other end 35 there is a sharp tip 36 that is typically beveled, serrated, pronged, or otherwise created to facilitate penetration of the skin 22 or other tissues and or substances 23. In the present invention, the end 33 of needle shaft 31 is configured to have a generally spherical ball 37 formed thereon. As shown in FIGS. 3 and 6 and most specifically in FIGS. 3D and 6C, hub 32 comprises a one-piece cap. Ball 37, as shown, fits into a socket 38 that is formed into hub or cap 32. The lumen 34 of needle 31 continues into and through spherical ball 37, providing a continuity of path 34 for fluid delivery or extraction by a needling system (not shown). FIGS. 3, 3A, 3B, 3C and 3D depict the needle shaft 31 and associated generally spherical ball 37 in an orientation such that the centerline 19 of the needle shaft 31 is aligned with the centerline 39 of hub or cap 32.

Figures 3E, 3F:
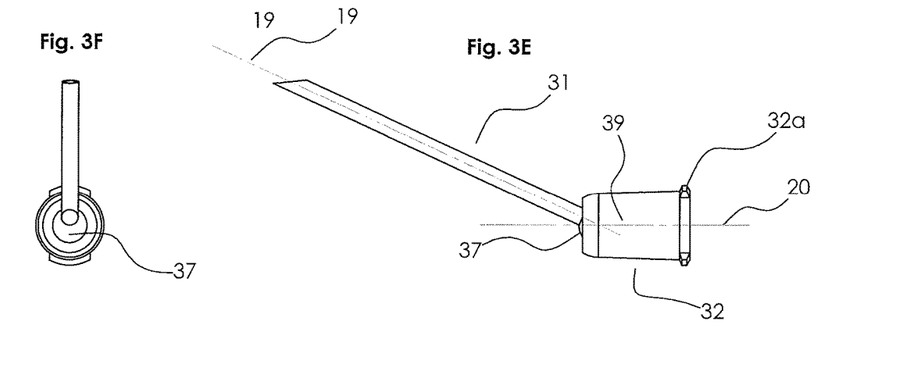
FIG. 3E is a front elevational view of the hollow needle embodiment shown in FIG. 3 with the needle position in a non-co-axial position.
FIG. 3F is a left side view of the hollow needle of FIG. 3E.

Now referring to FIGS. 3E and 3F, to provide access to certain points of interest that are inaccessible if the centerline 2 of syringe 11 is positioned coaxially with centerline 19 of the needle shaft 31, spherical ball 37 and socket 38 allow needle shaft 31 to be oriented in a non-coaxial manner with hub 32, while providing a seal between the hub 32 and the needle shaft 31, as will be explained below. Due to the nature of this ball and socket, the non-parallel nature of the needle shaft 31 relative to the syringe 11 can be adjusted by the user to provide optimal accessibility to the point of interest. It should be noted that although this example is shown with needle shaft 31 being a straight shaft, the ball and socket configuration shown can also be applied to non-straight needles, there by further enabling ease of accessibility to difficult to access points of interest. While in all of the above examples, the needling system 10 has included a syringe, it will be understood by persons having ordinary skill in the art that any device that can be associated with a needle and hub, including but not limited to IV devices, catheters, catheter introducers and others, without departing from the novel scope of the present invention.

Figure 4:
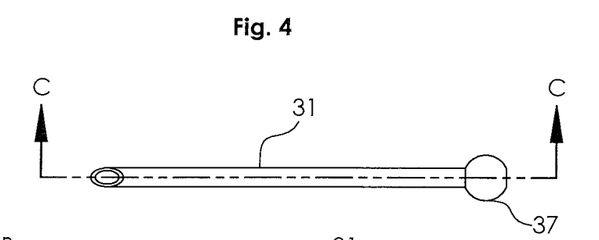
FIG. 4 is a top elevation view of the needle and ball component of FIG. 3.
Figure 4A:
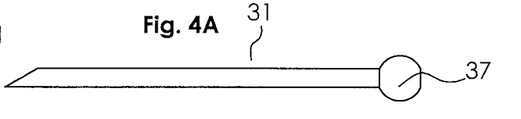
FIG. 4A is a front view of the device of FIG. 4.
Figure 4B:
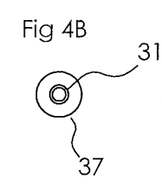
FIG. 4B is a left view of the device of FIG. 4A.
Figure 4C:
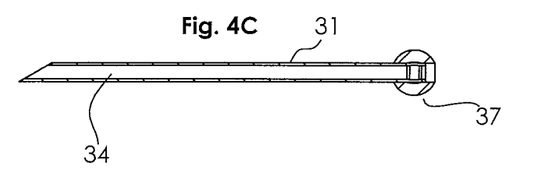
FIG. 4C is a cross-sectional view of the device of FIG. 4 taken along the line C-C.
Figure 5:
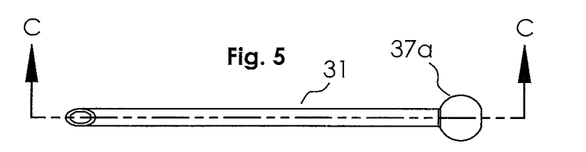
FIG. 5 is a top elevational view of another embodiment of the needle and ball component of the present invention.
Figure 5A:
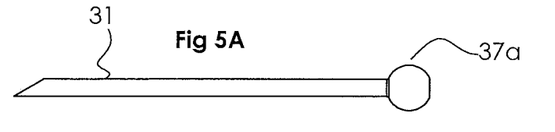
FIG. 5A is a front elevational view of the device of FIG. 5.
Figure 5B:
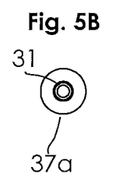
FIG. 5B is a left side view of the device of FIG. 5A.
Figure 5C:
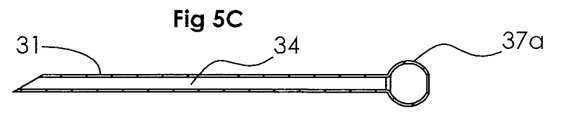
FIG. 5C is a cross-sectional view of the device of FIG. 5 taken along the line C-C.

Referring now to FIGS. 4 and 5, there are shown embodiments of the needle shaft 31 with associated spherical ball 37. In the creation of the needle and ball, one method, illustrated in FIG. 4, is to form the spherical ball 37 over needle shaft 31 by a casting means where, for example the ball may be made of plastic, metal or other appropriate material as required for the specific application. In another embodiment, shown in FIG. 5, the method of manufacture is to form the spherical ball 37 from the same tube that is used for the needle shaft 31 in a manner known to persons having ordinary skill in the art. In other embodiments, the needle and ball can be made of any desirable materials and the needle can be swaged to the ball, could be welded thereto or could be attached by adhesives. It will be understood by those with ordinary skilled in the art that these examples of a means of producing a hollow shaft with a spherical ball meant to be illustrative of ways of doing this and not meant to be a limitation on the method of creation, as there are a variety of other manufacturing and assembly methods that can be used to accomplish the desired result, without departing from the novel scope of the present invention.

Figure 6C:
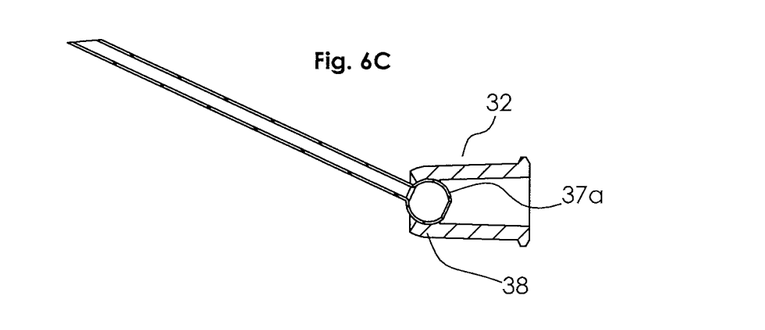
FIG. 6C is a cross-sectional view of the device of FIG. 6A taken along the line C-C.

Referring now to FIG. 6, and particularly to FIG. 6C, it can be seen how the one embodiment of a formed spherical ball 37a can integrate with socket 38 of hub 32 to provide the same non-parallel and non-axial conditions described above.

Figures 7, 7A:
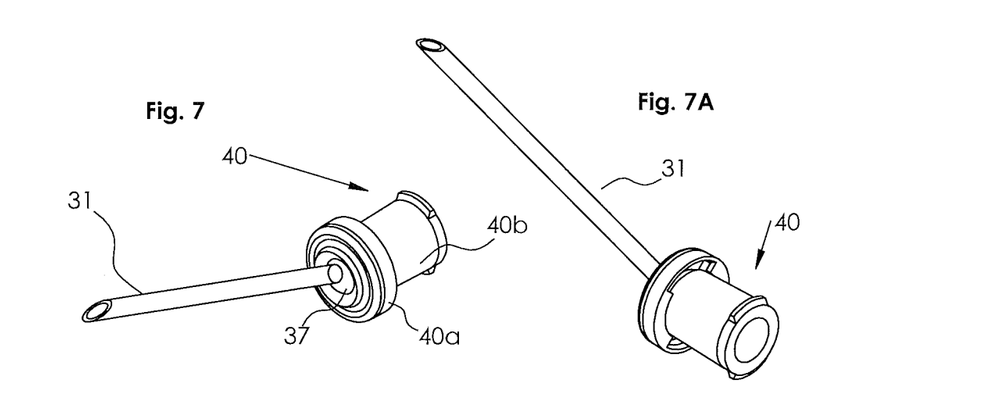
FIG. 7 is a perspective view of a position-locking embodiment of the present invention showing the needle in a non-coaxial orientation.
FIG. 7A is an alternative perspective view of the position locking embodiment of the present invention, with the needle in a non-coaxial orientation and showing details of the locking mechanism.
Figures 7B, 7C, 7D, 7E:
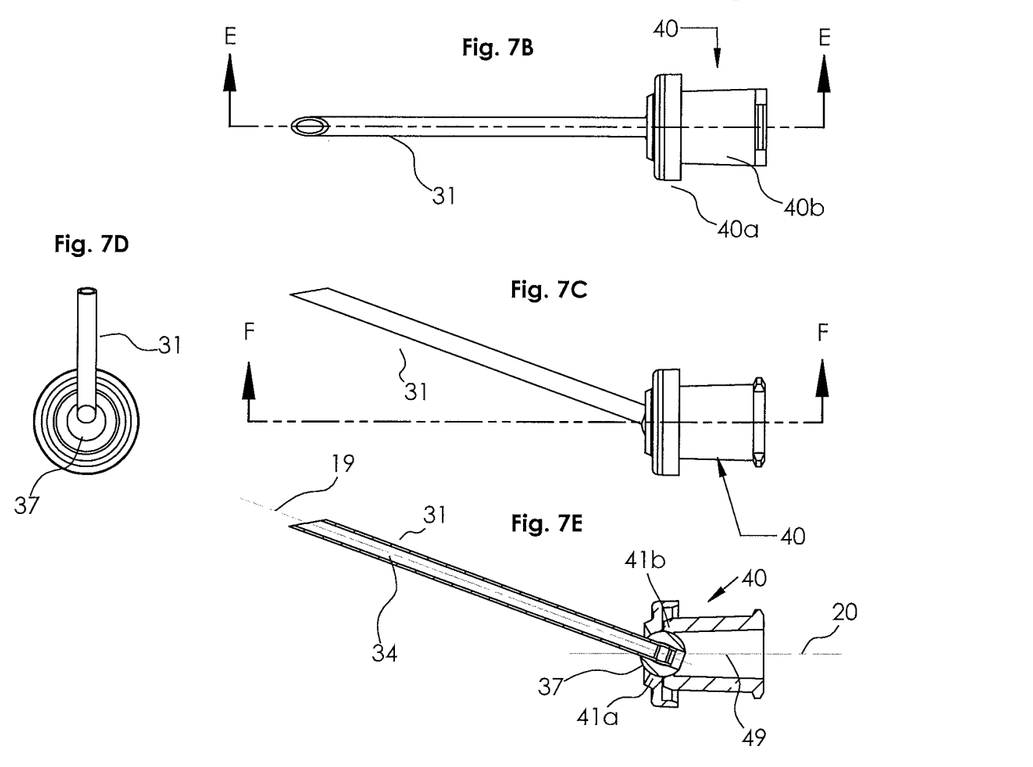
FIG. 7B is a top elevational view of the device of FIGS. 7 and 7A.
FIG. 7C is a front elevational view of the device FIG. 7B.
FIG. 7D is a left side view of the device of FIG. 7C.
FIG. 7E is a cross-sectional view of the device of FIG. 7B through line E-E.
Figure 7F:
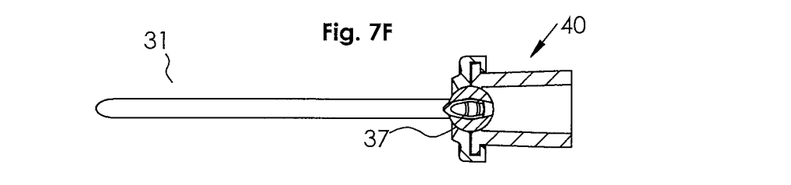
FIG. 7F is a cross-sectional view of the device of FIG. 7C through line F-F.
Figure 7G:
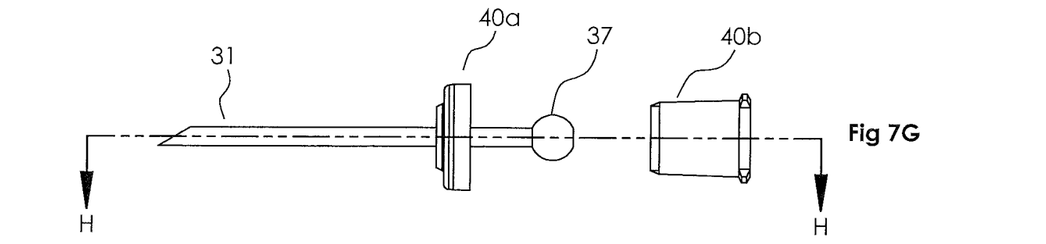
FIG. 7G is an exploded elevational view of the device of FIG. 7.
Figure 7H:
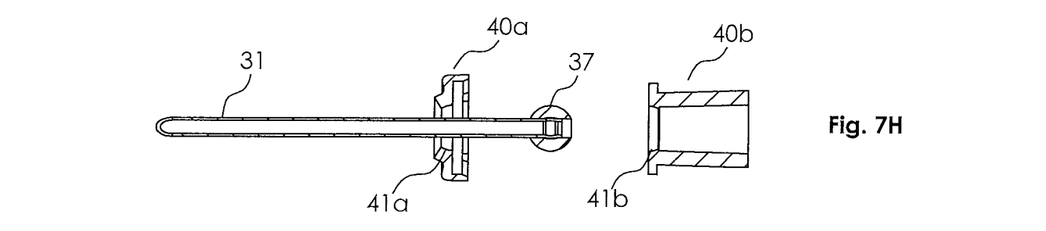
FIG. 7H is a cross-sectional view of the device of FIG. 7G, taken along the line H-H.
Figure 7I:
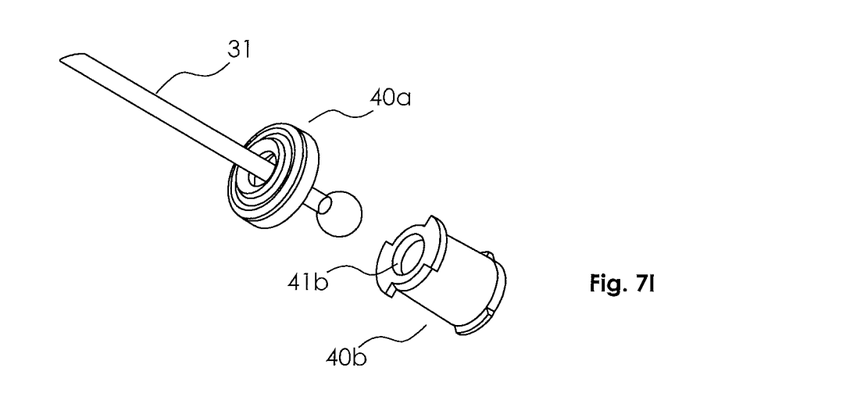
FIG. 7I is an exploded left perspective view of another embodiment of the device of FIG. 7.
Figure 7J:
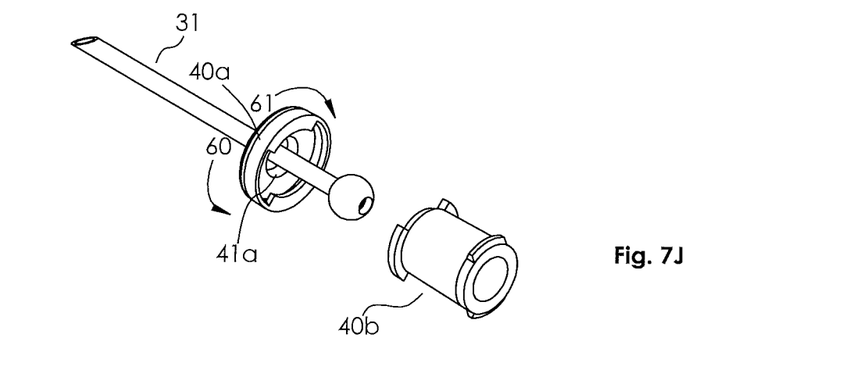
FIG. 7J is an exploded right perspective view of the device of FIG. 7I.
Figure 8:
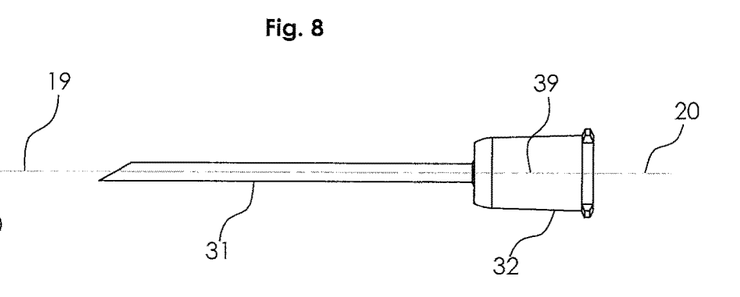
FIG. 8 is an elevational view of a needling system.
Figure 8A:
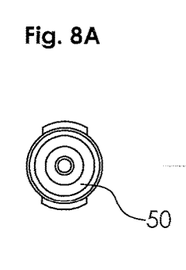
FIG. 8A is a left side view of the needling system of FIG. 8.

Now referring to FIG. 7, a spherical ball 37 and socket 38 within hub 40 provide a means for altering the angular position of centerline 19 of shaft 31 relative to centerline 39 of hub 40 and thereby centerline 20 of syringe 11; providing the user with enhanced capabilities for accessing the point of interest 24 as will be described below. It will be understood that a needling system made in accordance with this embodiment provides capability for the user to set and lock the orientation of centerline 19 of needle shaft 31 relative to centerline 49 of hub 40 and thereby centerline 20 of syringe 11. As shown in FIGS. 7G through 7J, hub 40 is comprised of two parts, locking ring 40a, which comprises part of socket 41 and acts to retain the needle shaft 31, and ball 37 seated in hub 40 and Luer fitting 40b, of hub 40, which comprises the other part of the socket 41b. It will be seen that locking ring 40a, of hub 40, is connected with Luer fitting 40b and that they act together to comprise the socket 41 which in use contains spherical ball 37 within hub 40 and provides fluid sealing for the fluid pathway through lumen 34. As illustrated, the rotation of locking ring 40a around hub axis 49 in a first direction cause the locking ring socket half 41a to move closer to Luer fitting socket half 41b thereby tightly clamping ball 37 between the two socket halves and locking the orientation of the needle shaft 31 to hub 40 and thereby syringe 11 (not shown). Rotation of locking ring 40a around hub axis 49 in a second opposite direction, see FIG. 7J, causes the locking ring socket half 41a to move further from the Luer fitting socket half 41b thereby loosening the pressure on the clamping ball and allowing adjustment of the orientation of the needle shaft 31 to hub 40 and thereby syringe 11. In operation, the rotation of locking ring 40 about socket half 41a will typically not allow the elements to be separated, such separation is shown in the exploded view for clarity. Persons having ordinary skill in the art will recognize that other methods of compressing the ball within the socket to create a friction fit that secures an angel for the needle can be incorporated into the device and method of the present invention without departing from the novel scope. The locking of the hub can be done in various ways to accomplish the securing of the angle of the needle in needling systems.

Figure 9:
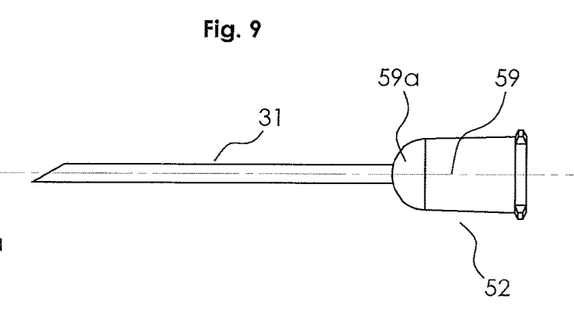
FIG. 9 is a front elevational view of a planar positioning embodiment of the present invention with the needle component in a coaxial orientation.
Figure 9A:
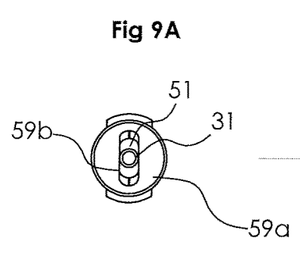
FIG. 9A is a left side view of FIG. 9.
Figures 9B, 9C:
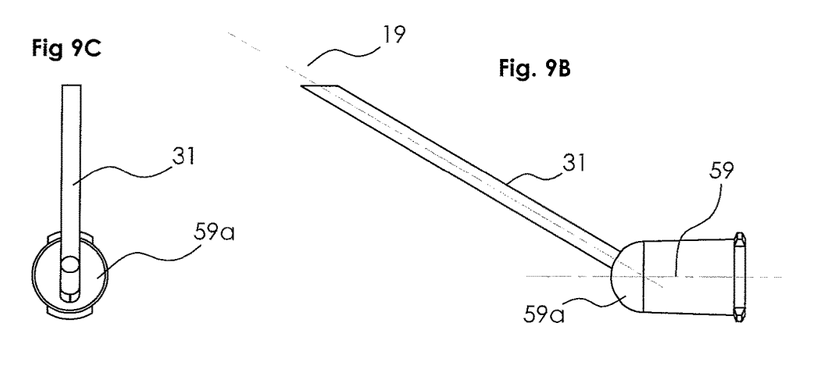
FIG. 9B is a front elevational view of a planar positioning embodiment of the present invention with the needle component in a non-coaxial orientation.
FIG. 9C is a left side elevational view of FIG. 9B.

Referring now to FIGS. 8, 8A, 9, 9A, and 9B, it will be seen that whereas hub 32 is created with a socket 38 (referring back to FIGS. 3D, and 6C), this geometry creates an opening 50 in the hub end and thereby allows unlimited directional movement of the needle shaft 31 within that opening. To limit the directions that the needle shaft 31 can be positioned, hub 52 can be fabricated with an oblong opening 51 thereby limiting angular travel of needle shaft 31 to one plane. FIG. 9 shows a variation of this arrangement wherein hub 59 comprises a hooded element 59a which forms a oval opening 59b through which needle can then only be rotated in one plane generally perpendicular to the centerline 19 of the needle shaft. In this manner less rotation and more control is provided to the user. It will be understood, that hood 59a can be made rotatable about hub 59 such that the plane of rotation can be changed as desired. While hood 59a is shown as semi-spherical this is done for illustrative purposes and other shapes can be incorporated to provide the limited scope of movement of the present embodiment without departing from the novel scope of the present invention.

Figure 10:
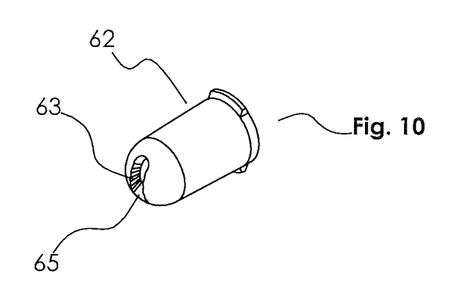
FIG. 10 is a perspective view of another embodiment of the hub of the present invention.
Figure 10A:
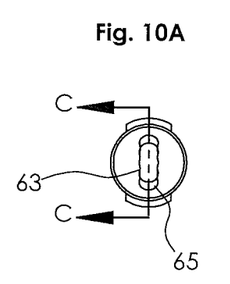
FIG. 10A is a front elevational view of the hub of FIG. 10.
Figure 10B:
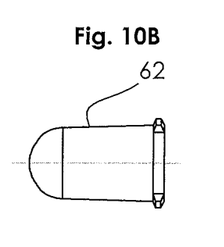
FIG. 10B is a side elevational view thereof.
Figure 10C:
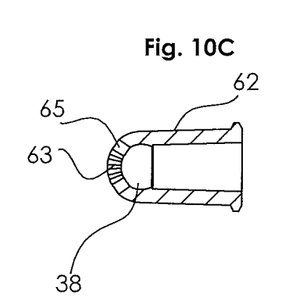
FIG. 10C is a cross-sectional view of the hub of FIG. 10, taken along the line C-C of FIG. 10A.
Figure 11:
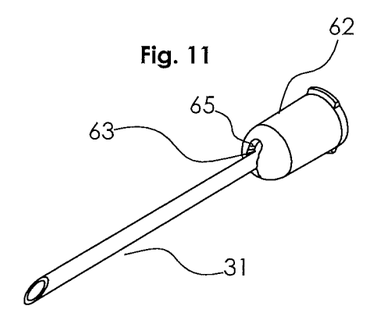
FIG. 11 is a perspective view of the hub of FIG. 10 with a needle therewithin in a first position.
Figure 11A:
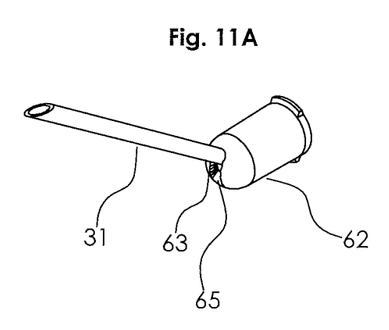
FIG. 11A is a second perspective view of the hub of FIG. 10 with a needle therewithin in a second position.

It will be understood that variations of the hub and needling system shown above can be made to provide more control of the position of the needle in use. For example in FIGS. 10, 10A, 10B and 10C, a variation of the hub 59 described above is shown. In FIG. 10, hub 62 is shown as having a frictional field 63 at the curve of the arced opening 65. In some embodiments the frictional field 63 can be a roughened surface and in other embodiments a scalloped pattern can be incorporated into the walls of arced opening 65. Persons having ordinary skill in the art will understand that a roughened opening can create a plethora of stop positions for a needle 31 so that the user can place the needle in the desired position to achieve the desired goal; while the use of a scalloped edge would create discrete stops within the arc to provide a set number of desirable positions. In the illustrative embodiment, the scallop pattern 63 shown in FIGS. 10, 10A and 10C, creates discrete positions that are predefined by the shown scalloped pattern 63 where the needle 31 can be moved to; in the illustrative embodiment, to any of 5 discrete positions. It should be noted that the present invention is meant to cover at least the minimum limiting case of at least two needle positions shown in FIGS. 11 and 11A, the first of which might be the position of co-axial or parallel centerlines of the hub and needle (FIG. 11) and the second is some no-coaxial and non-parallel position (FIG. 11A). A person having ordinary skill in the art will recognize that the scallop pattern 63 and the roughened surface 63 are but two of a multitude of ways to provide discrete positions that can be created without departing from the novel scope of the present invention, including, but not limited to, for example bevels, divots, indentations or grooves.

Benefits of adjusting needle between coaxial alignment with the syringe to non-parallel position of the syringe will be obvious to persons having ordinary skill in the art. For example, one such benefit is that the aligned position can be used to draw medicine from a container then the position can then be changed to a non-aligned (non-parallel) orientation to provide ease of access to the point of interest that might otherwise be restricted from access.

One simple example, to show the improved results of using the present invention, is in the treatment of stenosing tenosynovitis, commonly known as trigger finger. As is known, the tendons that bend the fingers glide easily with the help of the annular ligaments or pulleys. Annular ligaments are fibrous sheaths that are thick and strong as required by the repetitive use that such a system by nature necessitates. Trigger finger occurs when the pulley becomes too thick, such as through swelling due to repetitive use injury, so that the tendon cannot glide easily through the pulley; this often manifests itself in a finger that is locked in place, in a "trigger-like" shape. Traditional treatments of trigger finger include surgery, to open a section of the thick and fibrous pulley so as to allow the easier passage of the tendon therein and injection of a steroid to reduce the swelling. Oftentimes a doctor will first choose to provide an injection of a steroid between the tendon and pulley to reduce the swelling of the tendon and allow the tendon to glide through the pulley before considering surgery. In conventional treatment, a doctor will use a straight needle to inject into the finger, in a generally perpendicular motion relative to the finger, through the pulley and tendon and often to the bone. In this method, the patient will then wiggle the subject finger to allow the doctor to retract the needle, knowing to stopping the retraction when the syringe attached to the needle no longer wiggles with the finger. The lack of wiggle in the syringe then is an indication that the needle is no longer in the tendon and therefor is in the precise position, such that the doctor can inject the medicine in the space between the tendon and pulley.

This technique is problematic in that damage is done to the pulley and tendon by being pierced with the needle and the patient is subjected to pain. A better technique would be to use the same needle to pierce the finger in a generally horizontal manner and then drive the needle between the pulley and tendon. It will be understood, however, that a straight needle will not work for this, due to the angles that the needle will need to take, as a result of the compactness of the tendon and pulley system. Such methods are also exasperated when, for example, the finger is locked in the trigger position.

We have discovered that the needling system of the present invention, which as described above, can pierce the skin at one location and as a result of its configuration, be driven around the impediment to provide an appropriate dose of medicament to the exact location of the problem. Such an action can provide relief with a single treatment and not damage the pulley or tendon. The angular direction in the needle system of the present invention provides an appropriate angle to pierce the skin and drive, generally horizontally, between the tendon and pulley and there deliver the medicament where needed. Little or no damage is then done to the pulley or tendon, and the patient has less discomfort; as a result, treatment is completed more quickly and is more effective.

In the treatment of trigger finger it will be understood that a finger so affected is often caused, by the condition, to be bent so that the finger itself is a barrier to an injection between the pulley and the tendon. The bent condition, as is known to persons having medical experience, typically results because the swollen or enlarged part of the tendon is trapped within the thick and fibrous pulley such that a needle cannot reach the location of the swelling, both because of the position of the finger (bent back over the palm of the hand) and because the point of interest is within the pulley.

In the use of the injection, it will be understood that because of the position of the finger, bent above the point of interest, and the pulley, which is thick and fibrous, each comprise a blockage of the space between the pulley and the tendon. For this reason, it is often the case that the space cannot be reached using the conventional treatment protocols noted above, resulting in the need for more than one treatment; causing more damage to the pulley and the tendon in an effort to provide sufficient medicament to arrive at the desired result. When the space cannot be reached, treatment may require surgery with all of the attendant issues and problems of surgery.

Although an illustrative embodiment of the invention has been shown and described, it is to be understood that various modifications and substitutions may be made by those skilled in the art without departing from the novel spirit and scope of the invention.

What is claimed is:

1. A needling system, comprising:
a hollow needle having a distal end and a proximal end, the proximal end being ball-shaped and the needling system being workably configured to inject, or withdraw fluids through the hollow needle;
the needle comprises a section defining a first opening and a sharpened point defining a second opening with a shaft therebetween, the needle having at least one lumen extending from the upper section to the sharpened point;
a hub comprising a generally cylindrical shaped, one-piece cap, open at its ends, having an outer surface and an inner surface, the inner surface of the cap alone defining a ball-shaped socket seat, configured to retain the ball-shaped end of the needle, at its distal end, the hub having a connection element receptive to connection to any device that can attach to the hub to contribute to either pushing matter out through the hub and the needle, or drawing matter into the needle and the hub at a proximal end of the hub, the hub and the needle sharing a longitudinal axis therethrough when connected and in a first coaxial position;
the ball-shaped end of the needle being retained, in workable configuration, in the socket seat within the cap, retaining the hollow needle against transverse movement along the length of the longitudinal axis of the hub but allowing the ball-shaped end to rotate within the socket seat at all times including during use of the needling system, wherein the needle, extending out of the hub, is rotatable about its ball-shaped end, such that the distal end of the needle can be angled away from the longitudinal axis of the hub by pushing against the distal end of the needle, then can be immediately angled away, to a another position remaining workably configured and can inject or withdraw fluids continuously throughout such angular changes; and,
the hub further comprises a locking ring cooperatively attachable to the socket seat at the distal end of the hub, the locking ring and the cooperative socket seat each comprise cooperative inclined planes such that when the locking ring is twisted relative to the socket seat the locking ring and the socket seat are alternatively pushed together or pulled apart depending on a direction of rotation, such that when the ball-shaped end with the needle attached thereto is placed in the socket seat and the locking ring is twisted against the socket seat, the ball-shaped end is forced against the socket seat locking the needle in place in a selected position.

2. The needling system of claim 1, wherein the hub comprises a means for locking an angular position of the needle relative to the hub.

3. The needling system of claim 2, where the means for locking comprises means to confine rotation to a single plane relative to a main axis of the needling system.

4. The needling system of claim 3 wherein the means to confine rotation comprises a generally spherically shaped hood having a needle width slit therein, the slit being made generally perpendicular to the longitudinal axis of the hub, wherein when the hood and the needle are attached to the hub the needle can be pivoted away from the longitudinal axis only within the slit.

5. The needling system of claim 4, wherein the hood comprises an inner surface adjacent to the needle, the inner surface having one or more frictional protrusions to help prevent movement of the needle once set to a desired position relative to the longitudinal axis of the hub.

6. The needling system of claim 1 where the hub comprises a geometry that tends to limit an angular position of the needle, relative to the longitudinal axis of the hub, to positions within a generally conical shape about an edge of the hub.

7. The needling system of claim 1, where the hub comprises means to limit movement of the needle to an angular position in a single plane relative to a main axis of the needling system.

8. The needling system of claim 7 wherein the means to limit the movement of the needle comprises a generally spherically shaped hood having a needle width slit therein, the slit being made generally perpendicular to the longitudinal axis of the hub, wherein when the hood, the needle and the ball are attached to the hub the needle can be pivoted away from the longitudinal axis only within a plane of the slit.

9. The needling system of claim 8, wherein the slit comprises walls having a roughened surface to provide a frictional force to keep the needle at a discrete position relative to a main axis of the needling system within a plane of the slit.

10. The needling system of claim 8, wherein the slit comprises walls having a scalloped patterned surface to allow the needle to be locked in a discrete position relative to a main axis of the needling system within a plane of the slit.

* * * * *